United States Patent
Brasack et al.

(10) Patent No.: US 6,944,573 B2
(45) Date of Patent: Sep. 13, 2005

(54) METHOD AND APPARATUS FOR THE ANALYSIS OF SCRATCHES ON SEMICONDUCTOR WAFERS

(75) Inventors: Ingo Brasack, Dresden (DE); Marco Beckmann, Ilmenau (DE)

(73) Assignee: Infineon Technologies AG, Munich (DE)

( * ) Notice: Subject to any disclaimer, the term of this patent is extended or adjusted under 35 U.S.C. 154(b) by 89 days.

(21) Appl. No.: 10/740,377

(22) Filed: Dec. 18, 2003

(65) Prior Publication Data

US 2004/0220754 A1 Nov. 4, 2004

(30) Foreign Application Priority Data

Dec. 23, 2002 (DE) .......................................... 102 60 817

(51) Int. Cl.⁷ ................................................. G06F 11/30
(52) U.S. Cl. ...................................... 702/183; 702/182
(58) Field of Search .......................... 356/237.1, 237.2, 356/237.3, 237.4, 237.5; 438/16; 702/182, 183, 185, 189, FOR 135, FOR 137; 716/4

(56) References Cited

U.S. PATENT DOCUMENTS

| | | | | |
|---|---|---|---|---|
| 5,913,105 A | * | 6/1999 | McIntyre et al. | 438/16 |
| 6,407,373 B1 | * | 6/2002 | Dotan | 250/201.3 |
| 6,493,645 B1 | * | 12/2002 | Hladschik | 702/81 |
| 2004/0036863 A1 | * | 2/2004 | Matsusita et al. | 356/237.2 |

* cited by examiner

Primary Examiner—Bryan Bui
Assistant Examiner—Douglas N. Washburn
(74) Attorney, Agent, or Firm—Moser, Patterson & Sheridan, L.L.P.

(57) ABSTRACT

For the analysis of scratches on semiconductor wafers, the semiconductor wafer surface is detected and a possible scratch position or a scratch course on the semiconductor surface is determined, in which case a parameter value identifying the scratch is determined from the scratch position and the scratch course and this parameter value that has been determined is correlated with comparison parameter values, which identify installation-specific scratch positions and scratch courses, in order to determine an installation causing the scratch.

21 Claims, 1 Drawing Sheet

METHOD AND APPARATUS FOR THE ANALYSIS OF SCRATCHES ON SEMICONDUCTOR WAFERS

CROSS-REFERENCE TO RELATED APPLICATIONS

This application claims foreign priority benefits under 35 U.S.C. §119 to co-pending German patent application 102 60 817.2-52, filed Dec. 23, 2002. This related patent application is herein incorporated by reference in its entirety.

BACKGROUND OF THE INVENTION

1. Field of the Invention

The invention relates to a method and an apparatus for the analysis of scratches on semiconductor wafers.

2. Description of the Related Art

Electronics is nowadays dominated by microelectronic components with integrated circuits. Such integrated circuits represent a functional unit, which are characterized by a multiplicity of electronic functional elements having dimensions in the micron and sub-micron range and which are electrically and mechanically inseparably connected to one another. The electronic functional elements are realized on a common semiconductor substrate.

The fabrication of integrated circuits is essentially subdivided into three large stages: the production of the semiconductor slice (substrate), the fabrication of the individual chips on the semiconductor slice, also called the wafer hereinafter, and the final mounting of the individual chips. In this case, the standard method for producing the chips on the semiconductor slice is the planar technique. This is understood to be the simultaneous production of a large number of functional elements and the electrical interconnection thereof on a planar semiconductor slice. The individual steps can be classified in four large process groups, namely layer production, lithography, etching and doping, the process groups in each case preferably being processed in the aforesaid order in multiple cyclic repetition.

Several hundred individual steps are necessary to form large scale integrated circuits in the context of chip fabrication, in which case the semiconductor slices, or groups of semiconductor slices, also called batches hereinafter, often have to be transferred between the process installations that perform the respective individual steps, this usually being effected with the aid of automatic handling and mounting units. During this transfer of the semiconductor slices or of the batches with semiconductor slice surfaces, defects may arise on the semiconductor slices. According to experience, 0.1% of the wafers are damaged by the handling of the wafers in the process installations or during the transport between the process installations. In particular, the handling units often cause large scratches on the rear sides of the wafers during the transfer of the wafers, which scratches may bring about wafer fractures and thus a stoppage of the process installation. Such a stoppage of the process installations then leads to the outage of fabrication capacity and at the same time to the loss of the wafer. Defects caused by the process installations are also increasingly gaining in importance because the diameters of the semiconductor slices, and thus the risk of fracture, are increasing. Furthermore, for cost reasons it is an objective to continually increase the wafer throughput in chip fabrication.

In order to minimize the disturbance in chip fabrication on account of production-installation-specific scratches, in particular on the rear side of wafers, it is necessary to rapidly and actively search for causes and to correspondingly detect defects, in particular scratches. Hitherto, the search for causes has been effected by means of a surface inspection of the processed semiconductor slices and the subsequent attempt to correlate the defects that occur with the process installations causing the defects. However, such installation correlation proves to be difficult in particular when a fault image occurs only at a small number of wafers. In order to determine the fault cause, it is furthermore possible to carry out test runs with bare slices in order to determine the process installation causing the fault. However, this is time-consuming and expensive and furthermore leads to a production installation stop during chip fabrication.

SUMMARY OF THE INVENTION

It is an objective of the invention to provide a method and an apparatus for rapidly searching for causes and monitoring defects on wafers, in particular scratches on rear sides of wafers, and thereby to achieve a faster elimination of faults and reduction of rejects or reworking.

According to the invention, for the analysis of scratches on semiconductor wafers, the semiconductor wafer surface is scanned and a possible scratch position or a scratch course on the semiconductor surface is determined. A parameter value identifying the scratch is then determined from the scratch position and the scratch course and this parameter value is correlated with comparison values, which identify installation-specific scratch positions and scratch courses, in order to determine an installation causing the scratch.

This process according to the invention of searching for scratch causes on wafers makes it possible to rapidly and simply determine a process installation causing a scratch. As a result, there is no need for a complicated search for causes by installation correlation in the context of a batch comparison and complicated test runs with bare slices. At the same time, it is possible largely to dispense with a production installation stop during wafer fabrication and thus to avoid capacity losses through additional installation monitoring.

According to the invention, it is preferred to determine the parameter value identifying the scratch position and the scratch course on the semiconductor wafer surface in such a way that a straight line for the approximation of the scratch course is defined through the two end points of the detected scratch and the perpendicular distance between the center point of the semiconductor wafer slice and the straight line defining the scratch course is determined as the parameter value. This procedure enables a rapid and simple definition of a parameter for the correlation of scratches with process installations. The complexity for determining the parameter and thus the subsequently required comparison complexity for defining the installation causing the scratch can be reduced to a minimum. The mathematical complexity for defining the scratch parameter is minimal.

This applies in particular when, according to a preferred embodiment, for determining the perpendicular distance—defining the parameter value—between the center point of the semiconductor wafer slice and the straight line defining the scratch course, a procedure is chosen in which three points are determined on a circle circumference of the semiconductor slice, in which case two of the three points correspond to the end points of the scratch essentially tangentially lengthened on the circle circumference. Defining three points makes it possible to rapidly and simply calculate the wafer center point and radius and from the latter, in turn, the perpendicular distance of the straight line representing the scratch from a simple three-point coordinate detection. This procedure provides for a particularly simple and rapid detection of scratches on wafer surfaces.

BRIEF DESCRIPTION OF THE DRAWINGS

The invention is explained in more detail with reference to the accompanying drawings, in which.

DETAILED DESCRIPTION OF THE PREFERRED EMBODIMENT

Figure 1:
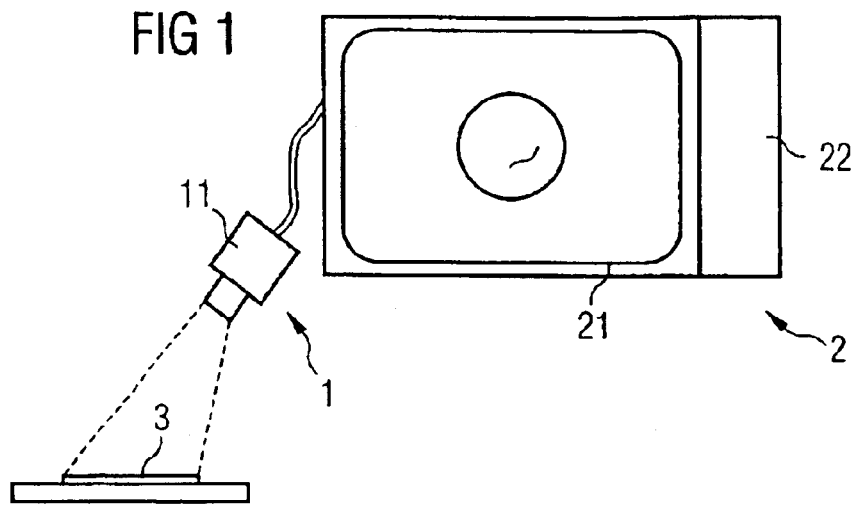
FIG. 1 shows an analysis device according to the invention for the monitoring of scratches on semiconductor wafers and for finding causes.

The apparatus according to the invention for scratch analysis is composed of a surface scanning device 1 and an analysis device 2 with screen 21. The scanning device 1 is preferably an optical scanning unit for automatically scanning a wafer surface 3. In this case, as is illustrated in FIG. 1, the wafer surface 3 is preferably detected optically by means of a camera 11 in a pass, in order not to obstruct the wafer flow during chip fabrication. However, instead of an optical detection, as shown in FIG. 1, it is possible to use any known method for scanning a surface. Scanning data are supplied to the analysis device 2 by the scanning device 1, which analysis device represents the scanned wafer surface on a screen 21. The wafer surface 3 is reproduced in enlarged fashion in FIG. 2.

Figure 2:
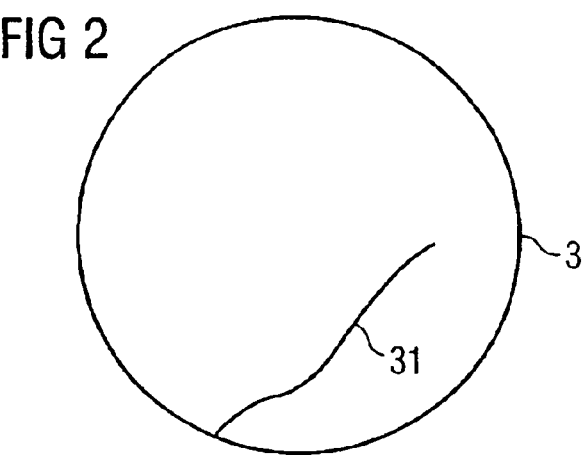
FIG. 2 shows an image of a rear side of a wafer with a scratch, recorded by the apparatus according to FIG. 1.

FIG. 2 shows that there is a long scratch 31 on the wafer surface 3. In order to determine the cause of this scratch 31, according to the invention, in the data processing unit 2, a parameter identifying the scratch 31 is determined and compared with previously stored parameter values, which identify installation-specific scratch positions and scratch courses, in order to ascertain a process installation causing the scratch during the wafer processing.

Scratches are generally caused by parts of process installations which touch wafers, e.g., handlers or prealigners. The scratch position and the scratch course are installation-specific in this case. Therefore, in the context of test runs, scratches that occur are correlated with the corresponding process installations and a comparison value identifying the respective scratch with regard to its position and its course is determined and is stored in a database device 22 in the analysis device 2.

Figure 3:
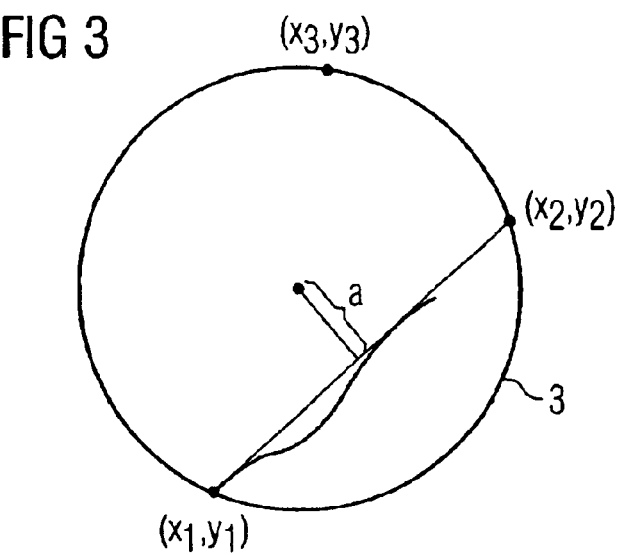
FIG. 3 shows a calculation method according to the invention for determining a parameter value identifying the scratch position and scratch course.

According to the invention, the distance between the scratch and the center point of the semiconductor slice 3 is preferably defined as the parameter for identifying the scratch position and the scratch course. For this purpose, as shown in FIG. 3, a straight line is placed through the two end points of the scratch 31 and the perpendicular distance (a) between the center point of the wafer slice and the straight line defining the scratch course is calculated. In this case, the two end points of the scratch may be defined automatically by the analysis device 2, e.g., automatically from the resulting contrast between the scratch and the wafer surface. However, it is also possible for an operator of the analysis device 2, e.g., to use a mouse to define the end points of the scratch on the wafer surface image 3 represented on the screen 21, as shown in FIG. 3. The calculation of the perpendicular distance (a) between the center point of the wafer slice 3 and the straight line defining the scratch course is in this case preferably defined from the coordinates of three points on the circumference of the wafer slice 3. In this case, two points $(x_1, y_1)$ $(x_2, y_2)$ correspond to the two end points of the scratch essentially tangentially lengthened on the circle circumference. The third point $(x_3, y_3)$ is an arbitrary further point on the circle circumference. From the coordinates of these points, it is possible to determine the radius and the center point of the wafer slice whose circumference runs through these points. In this case, the center point $(x_m, y_m)$ of the wafer slice can be calculated by means of the following simple formula:

$$y_m = [(x_3^2 - x_1^2 + y_3^2 - y_1^2)(x_2 - x_1) - (x_2^2 - x_1^2 + y_2^2 - y_1^2)(x_3 - x_1)]/2[(y_3 - y_1)(x_2 - x_1) - (y_2 - y_1)(x_3 - x_1)]$$

$$x_m = [(x_2^2 - x_1^2) + (y_2^2 - y_1^2) - 2y_m(y_2 - y_1)]/2(x_2 - x_1)$$

The distance between the straight line reproducing the scratch course and the center point of the wafer slice is a parameter that unambiguously identifies the scratch. Through comparison with prestored comparison values which are assigned to the scratches produced by specific process installations during chip production, an installation causing the scratch can be defined in a simple manner. During the comparison, for this purpose, the parameter value is correlated in prestored comparison values taking account of a permissible predetermined minimum deviation and the production installation associated with the correlated comparison value is then specified by the analysis device 2.

What is claimed is:

1. A method for analysis of scratches on semiconductor wafers, comprising:

scanning a surface of a semiconductor wafer having a scratch on the surface;

determining a geometric representation of the scratch;

determining a parameter value on the basis of the geometric representation and a point on the surface; and correlating the parameter value with comparison parameter values corresponding to pre-determined scratches caused by specific processing equipment, whereby a specific processing equipment can be identified as being responsible for causing the scratch on the surface of the semiconductor wafer.

2. The method of claim 1, wherein the point on the surface is the center of the surface, and wherein determining the representative course of the scratch comprises plotting a straight line between two selected points on the scratch, and wherein determining the parameter value comprises determining a length of a radial line originating from the center and orthogonally intersecting, and terminating at, the straight line.

3. The method of claim 1, wherein the point on the surface is the center of the surface and wherein determining the parameter value comprises determining a distance between the center of the semiconductor wafer and the geometric representation of the scratch.

4. The method of claim 3, wherein the geometric representation of the scratch is a straight line approximation of the scratch.

5. The method of claim 3, wherein the geometric representation of the scratch is a straight line approximation of the scratch being defined by a straight line plotted through two end points of the scratch and wherein the distance is determined mathematically using three points on a circumference of the semiconductor wafer.

6. The method of claim 5, wherein two of the three points are determined by the intersection of the straight line with the circumference of the semiconductor wafer and a third point of the three points is arbitrarily selected.

7. The method of claim 1, wherein determining the geometric representation of the scratch comprises determining a representative course of the scratch.

8. The method of claim 7, wherein determining the representative course of the scratch comprises plotting a straight line between two selected points on the scratch.

9. A method for analysis of scratches on semiconductor wafers, comprising:

scanning a surface of a semiconductor wafer having a scratch on the surface;

determining a geometric representation of the scratch, wherein the geometric representation is representative of at least a location of the scratch on the surface and a course of the scratch over the surface;

determining a distance between a center point of the surface and the course of the scratch, as represented by the geometric representation; and correlating the distance with comparison distance values corresponding to pre-determined scratches caused by specific processing equipment, whereby a specific processing equipment can be identified as being responsible for causing the scratch on the surface of the semiconductor wafer.

10. The method of claim 9, wherein determining the geometric representation of the scratch comprises plotting a straight line through at least two points located on the scratch.

11. The method of claim 10, wherein determining the distance comprises determining a length of a radial line originating from the center point and orthogonally intersecting, and terminating at, the straight line.

12. The method of claim 9, wherein determining the distance comprises determining coordinates of the center point on the basis of three points located on a circumference of the semiconductor wafer.

13. An apparatus for the analysis of scratches on semiconductor wafers, comprising:

a device for scanning a surface of a semiconductor wafer; and an analysis device configured to:

define a scratch position and a scratch course on the surface;

determine a parameter value identifying the scratch position and the scratch course;

correlate the parameter value identifying the scratch position and the scratch course with comparison values identifying equipment-specific scratch positions and scratch courses, which comparison values are stored in a memory; and determine a specific equipment causing the scratch on the basis of the correlation.

14. The apparatus of claim 13, wherein the analysis device defines the scratch position and the scratch course on the surface by defining a straight line through two end points of the scratch and determines the parameter value by determining a shortest distance between a center point of the wafer and the straight line defining the scratch course.

15. The apparatus of claim 14, wherein the analysis device defines the scratch position and the scratch course on the wafer surface by defining at least three points on a circumference of the wafer, wherein two of the three points correspond to intersections of the straight line with the circumference.

16. An apparatus for the analysis of scratches on semiconductor wafers, comprising:

a device for scanning a surface of a semiconductor wafer; and an analysis device configured to:

produce a representation of a scratch on the surface;

determine a parameter of the representation of the scratch;

compare the parameter to stored parameters of scratches made by specific equipment; and identify a specific equipment responsible for making the scratch on the basis of the comparison.

17. The apparatus of claim 16, wherein the parameter is a length.

18. The apparatus of claim 16, wherein the representation is course and position of the scratch and the parameter is a distance from a center of the surface to the representation of the scratch on the wafer.

19. The apparatus of claim 16, further comprising a storage device containing the stored parameters of scratches, wherein each stored parameter is associated with a particular piece of equipment.

20. The apparatus of claim 16, further comprising a storage device containing the stored parameters of scratches, wherein each stored parameter is associated with one of a plurality of pieces of equipment.

21. The apparatus of claim 20, wherein at least one of the plurality of pieces of equipment comprises a wafer handler.

* * * * *